US009771263B2

(12) United States Patent
Pokroy et al.

(10) Patent No.: US 9,771,263 B2
(45) Date of Patent: Sep. 26, 2017

(54) CRYSTALS OF SEMICONDUCTOR MATERIAL HAVING A TUNED BAND GAP ENERGY AND METHOD FOR PREPARATION THEREOF

(71) Applicant: TECHNION RESEARCH AND DEVELOPMENT FOUNDATION LTD., Haifa (IL)

(72) Inventors: Boaz Pokroy, Haifa (IL); Anastasia Brif, Haifa (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 95 days.

(21) Appl. No.: 14/500,775

(22) Filed: Sep. 29, 2014

(65) Prior Publication Data

US 2015/0090942 A1 Apr. 2, 2015

Related U.S. Application Data

(60) Provisional application No. 61/884,367, filed on Sep. 30, 2013.

(51) Int. Cl.
*H01L 29/167* (2006.01)
*H01L 29/207* (2006.01)
(Continued)

(52) U.S. Cl.
CPC ............. *C01B 19/007* (2013.01); *C01G 9/02* (2013.01); *C01G 11/02* (2013.01); *C01G 21/21* (2013.01); *G01N 33/588* (2013.01); *G01N 33/68* (2013.01); *H01L 29/167* (2013.01); *H01L 29/207* (2013.01); *H01L 29/2203* (2013.01); *H01L 29/227* (2013.01); *C01P 2002/74* (2013.01);
(Continued)

(58) Field of Classification Search
None
See application file for complete search history.

(56) References Cited

U.S. PATENT DOCUMENTS 6,110,273 A * 8/2000 Sanjoh ...................... C30B 7/00
117/68
6,921,496 B2 * 7/2005 Anderson .............. B82Y 15/00
252/301.33

(Continued)

OTHER PUBLICATIONS

Fonstad, C.G., "Lecture 1—The Compund Semiconductor Palette", dated Feb. 2003, MIT OpenCourseWare, slides 1-23, copy attached as a PDF; Accessed online at: http://ocw.mit.edu/courses/electrical-engineering-and-computer-science/6-772-compound-semiconductor-devices-spring-2003/lecture-notes/Lecture1v2.pdf.*
(Continued)

*Primary Examiner* — Katie L Hammer
(74) *Attorney, Agent, or Firm* — Knobbe Martens Olson & Bear LLP

(57) ABSTRACT

The present invention provides a semiconductor crystal comprising a semiconductor material having a tuned band gap energy, and methods for preparation thereof. More particularly, the invention provides a semiconductor crystal comprising a semiconductor material and amino acid molecules, peptides, or a combination thereof, incorporated within the crystal lattice, wherein the amino acid molecules, peptides, or combination thereof tune the band gap energy of the semiconductor material.

21 Claims, 5 Drawing Sheets
(4 of 5 Drawing Sheet(s) Filed in Color)

(51) Int. Cl.
| | |
|---|---|
| H01L 29/22 | (2006.01) |
| H01L 29/227 | (2006.01) |
| H01L 29/24 | (2006.01) |
| C01B 19/00 | (2006.01) |
| C01B 17/00 | (2006.01) |
| G01N 33/58 | (2006.01) |
| G01N 33/68 | (2006.01) |
| C01G 21/21 | (2006.01) |
| C01G 9/02 | (2006.01) |
| C01G 11/02 | (2006.01) |
| C07K 4/00 | (2006.01) |
| C07K 9/00 | (2006.01) |

(52) U.S. Cl.
CPC ............ *C01P 2006/40* (2013.01); *C07K 4/00* (2013.01); *C07K 9/00* (2013.01)

(56) References Cited

U.S. PATENT DOCUMENTS

| | | | | |
|---|---|---|---|---|
| 2001/0023078 | A1* | 9/2001 | Bawendi | B82Y 15/00 436/524 |
| 2005/0118631 | A1* | 6/2005 | Bawendi | B82Y 15/00 506/17 |
| 2006/0037177 | A1* | 2/2006 | Blum | B01D 9/005 23/296 |
| 2008/0009434 | A1* | 1/2008 | Reches | A61L 27/38 530/300 |
| 2011/0098445 | A1* | 4/2011 | Mattoussi | B82Y 15/00 530/333 |

OTHER PUBLICATIONS

Borukhin S., Bloch L., Radlauer T., Hill A.H., Fitch A.N. and Pokroy B. "Screening the incorporation of amino acids into an inorganic crystalline host: the case of calcite" Advanced Functional Materials. 22, pp. 4216-4224. (2012).

Guoqiang Q., Guanglei Z., Dongchun L., and Shimin L. "Lattice and internal relaxation of ZnO thin film under in-plane strain" Thin Solid Films, 519, pp. 378-384. (2010).

Muñnoz—Espí R., Qi Y., Lieberwirth I., Gómez C.M., and Wegner G.. "Surface—functionalized latex particles as controlling agents for the mineralization of zinc oxide in aqueous medium" Chemistry—A European Journal, 12, pp. 118-129. (2006).

Muñoz-Espí , R., Jeschke, G., Lieberwirth, I., Gómez, C.M., and Wegner, G., "ZnO-latex hybrids obtained by polymer-controlled crystallization: A spectroscopic investigation", Journal of Physical Chemistry B, 111, pp. 697-707. (2007).

Pokroy B., Caspi E. N., Quintana J. P., Berner A. and Zolotoyabko E. "Anisotropic lattice distortions in biogenic aragonite", Nature Materials, 4, pp. 900-902. (2004).

Pokroy B., Fitch A. N., Lee P. L., Quintana J. P., Caspi E. N. and Zolotoyabko E. "Anisotropic lattice distortions in mollusk-made aragonite: a widespread phenomenon", Journal of Structural Biology. 153, pp. 145-150. (2006).

Pokroy B., Fitch A. N., Mahn F., Kapon M., Adir N. and Zolotoyabko E., "Anisotropic lattice distortions in biogenic calcite induced by intra-crystalline organic molecules", Journal of Structural Biology, 155, pp. 96-103. (2006).

Pokroy B., Fitch A. N., and Zolotoyabko E., "The microstructure of biogenic calcite: a view by high-resolution synchrotron powder diffraction", Advanced Materials., 18, pp. 2363-2368. (2006).

Reynolds D.C., Look D.C., Jogai B., Litton C.W., Cantwell G., and Harsch W.C., "Valence-band ordering in ZnO", Physical Review B, 60 (4), pp. 2340-2344. (1999).

Srikant, V. and Clarke, D.R., "On the optical band gap of zinc oxide", Journal of Applied Physics 83 (10), pp. 5447-5451. (1998).

Yadav S.K., Sadowski T. and Ramprasad R. "Density functional theory study of ZnX (X=O, S, Se, Te) under uniaxial strain", Physical Review B, 81, pp. 144120-144125. (2010).

Peng J.W., Liu P.C. and Lee, S., "Reversible band gap tuning of metal oxide films using hydrogen and oxygen plasmas", Thin Solid Films, 531,pp. 81-87. (2013).

* cited by examiner

CRYSTALS OF SEMICONDUCTOR MATERIAL HAVING A TUNED BAND GAP ENERGY AND METHOD FOR PREPARATION THEREOF

CROSS-REFERENCE TO RELATED APPLICATIONS

The present invention claims the benefit of U.S. Provisional Patent Application No. 61/884,367, filed Sep. 30, 2013, the entire content of which being herewith incorporated by reference as if fully disclosed herein.

TECHNICAL FIELD

The present invention provides semiconductor crystals comprising semiconductor material having a tuned band gap energy, and methods for the preparation thereof.

BACKGROUND ART

Crystal formation in biological systems has attracted many researchers over the years because of the enhanced structural properties—mechanical (Fratzl and Weinkamer, 2007; Berman et al., 1990; Miserez et al., 2009; Weaver et al., 2012), optical (Levy-Lior et al., 2010; Levy-Lior et al., 2008) and magnetic (Kirschvink and Gould, 1981)—of its outcome compared to non-biogenic crystals. Arguably by far the most research in the field has been focused on biogenic calcium carbonate and its properties (Sommerdijk and de With, 2008; Weiner and Addadi, 2011; Dunlop and Fratzl, 2010; Estroff, 2008; Gower, 2008). Particular attention has been directed to biogenic calcite owing to its enhanced fracture toughness, shown to originate as a result of the deflection of propagating cracks away from the pronounced cleavage planes (Berman et al., 1988; Chernov, 2003). This is achieved by the presence of intracrystalline proteins and organic molecules within individual crystals in directions oblique to the (104) cleavage plane of calcite (Berman et al., 1988). These intracrystalline molecules have also been shown to strongly influence crystal shape, morphology (Aizenberg et al., 1996) and coherence length (Berman et al., 1993; Aizenberg et al., 1995). Another outcome of their presence is the existence of systematic anisotropic lattice strains (Pokroy et al., 2004; Pokroy et al., 2006a). We have shown that incorporation of proteins and even of single amino acids into calcite grown synthetically leads to similar lattice strains (Pokroy et al., 2006b; Borukhin et al., 2012). Kim et al. showed that by mimicking proteins with micelles or polymer particles that become incorporated into calcite it is possible to reproduce lattice strains and, moreover, to enhance hardness of the calcite (Kim et al., 2011; Kim et al., 2010). Similar results were obtained in a study by Schenk et al. using polyelectrolytes (Schenk, 2012). It was also shown that an agarose gel can be incorporated into single crystals of calcite (Li and Estroff, 2009). Colfen et al. showed that amino acids affect the early stages of calcium carbonate formation (Picker et al., 2012). A partial but deeper understanding of what governs the incorporation of biological molecules into calcium carbonate was recently achieved after mapping of the incorporation of the 20 common amino acids into synthetic calcite (Borukhin et al., 2012). As revealed by Wenger et al. with respect to crystallization of non-biogenic ZnO, the addition of synthetic latex particles can influence both the morphology as well as the optical and paramagnetic properties of the crystals due to latex incorporation (Muñoz-Espí et al., 2007; Muñoz-Espí et al., 2006).

SUMMARY OF INVENTION

It has now been surprisingly found, in accordance with the present invention, that amino acids can be incorporated into the crystal lattice of semiconductor crystals such as those made of ZnO, CdS or PbS, in a manner similar to that previously observed in calcite, and consequently induce lattice strains accompanying the incorporation that lead to systematic changes in the band gap of the semiconductor host.

In one aspect, the present invention thus relates to a semiconductor crystal comprising a semiconductor material having a band gap energy and amino acid molecules, peptides, or a combination thereof, incorporated within the crystal lattice, wherein said amino acid molecules, peptides, or combination thereof tune the band gap energy of said semiconductor material. In particular embodiments, the semiconductor material is a compound consisting of two or more chemical elements, e.g., a binary compound or a ternary compound consisting of two or three chemical elements, respectively.

In another aspect, the present invention provides a method for the preparation of semiconductor crystals as defined above, wherein said semiconductor material consists of two or more elements, said method comprising:
  (i) precipitating said semiconductor crystals from either
    (a) an aqueous solution containing said amino acid molecules, peptides, or combination thereof, and ions of said two or more elements; or (b) an aqueous solution containing said amino acid molecules, peptides, or combination thereof, and ions of at least one of said two or more elements, in the presence of precursors of the other of said two or more elements; and
  (ii) collecting the obtained semiconductor crystals.

According to the present invention, particular such methods are used for the preparation of such semiconductor crystals, wherein the semiconductor material is a binary or ternary compound.

BRIEF DESCRIPTION OF DRAWINGS

The file of this patent contains at least one drawing/photograph executed in color. Copies of this patent with color drawing(s)/photograph(s) will be provided by the Office upon request and payment of the necessary fee.

DETAILED DESCRIPTION OF THE INVENTION

Figure 1A:
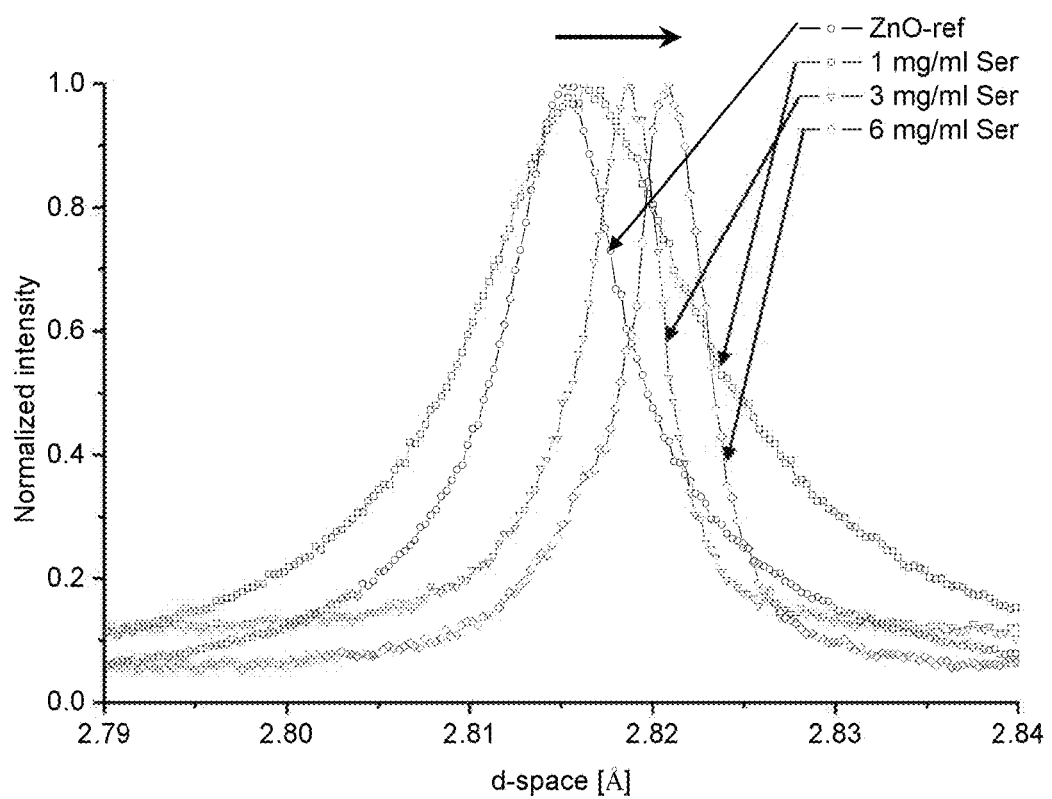
FIGS. 1A-1B show (100) XRD diffraction peaks of crystals of pure ZnO (ZnO-ref) and ZnO grown in the presence of 1, 3 or 6 mg/ml serine (Ser) (1A); and of crystals of pure ZnO and ZnO grown in the presence of 3 mg/ml serine before and after annealing at 300° C. for 90 min (1B).

Band gap engineering is of cardinal importance in various applications where a specific band gap value is required (Capasso, 1987), e.g., in laser diodes, solar cells, and heterojunction bipolar transistors. Tuning of the band gap can be achieved by (i) varying the chemical composition of the semiconductor material; (ii) strain engineering via epitaxial crystal growth; (iii) size confinement on the nanometer scale (Capasso, 1987); or (iv) a combination of these methods. A linear relationship has been shown to exist between the band gap of semiconductors and their lattice strain (Wei and Zunger, 1994; Guoqiang et al., 2010).

As found and shown in the Examples section hereinafter, the band gap energy of a semiconductor material can be engineered, i.e., tuned or altered, by incorporation of amino acid molecules within the crystal lattice of the semiconductor crystals, thereby inducing lattice strains that lead to systemic changes, i.e., marked shifts, in the band gap of the semiconductor host.

In one aspect, the present invention thus relates to a semiconductor crystal comprising (i) a semiconductor material having a band gap energy; and (ii) amino acid molecules, peptides, or a combination thereof, incorporated within the crystal lattice, wherein said amino acid molecules, peptides, or combination thereof tune the band gap energy of said semiconductor material. The incorporation of amino acid molecules, peptides, or combinations thereof with a semiconductor material according to the present invention, in fact, engineers the band gap of the semiconductor material, and can either increase or decrease the band gap energy of said semiconductor material.

The term "band gap energy" ($\Delta E_g$) or "energy gap", as used herein with respect to semiconductor materials, refers to the energy difference between the top of the valence band, i.e., the highest range of electron energies in which electrons are normally present at absolute zero temperature, and the bottom of the conduction band, i.e., the range of electron energies enough to free an electron from binding with its atom to move freely within the atomic lattice of the material as a "delocalized electron". While being able to jump from one band to another, in order for an electron to jump from a valence band to a conduction band, a specific minimum amount of energy is required for the transition, wherein the required energy differs with different materials. Electrons can gain that energy by absorbing either a phonon (heat) or a photon (light). The conductivity of intrinsic semiconductors, also called undoped semiconductors or i-type semiconductors, is strongly dependent on the band gap, wherein the only available charge carriers for conduction are those electrons that have enough energy to be excited across the band gap. Band gap engineering is the process of controlling or altering the band gap of a material by controlling the composition of the semiconductor.

A semiconductor material having a tuned band gap energy, as referred to herein, means a semiconductor material having a band gap energy that is different from that characterizing a reference sample of said semiconductor material, i.e., the reference band gap energy, and can be either increased or decreased compared to the reference band gap energy. As shown herein, the incorporation of amino acid molecules, peptides, or a combination thereof, within the crystal lattice of a semiconductor material, during the crystal growth, induces lattice strains and consequently tunes the band gap energy of the semiconductor material, wherein the difference between the tuned band gap energy and the reference band gap energy of said semiconductor material depends on the specific amino acid or peptide incorporated in the crystal lattice as well as the concentration of said amino acid or peptide in the aqueous solution from which the semiconductor crystals are precipitated.

In certain embodiments, the band gap energy of the semiconductor material composing the semiconductor crystals of the present invention is in the infrared, including the vis/near infrared, energy range. Examples of such semiconductor materials include, without limiting, PbS, PbSe, PbTe, CdTe, InN, InP, InAs, InSb, HgS, HgSe and GaSb.

In other embodiments, the band gap energy of the semiconductor material composing the semiconductor crystals of the present invention is in the visible energy range. Non-limiting examples of such semiconductor materials include CdSe, CdTe, ZnSe, ZnTe, AlAs, AlP, AlSb, AlN, GaP and GaAs.

In further embodiments, the band gap energy of the semiconductor material composing the semiconductor crystals of the present invention is in the ultraviolet energy range. Particular examples of such semiconductor materials include, e.g., GaN and ZnS.

In certain embodiments, the semiconductor material composing the semiconductor crystal of the present invention consists of two or more chemical elements.

In particular such embodiments, the semiconductor material is a binary compound, i.e., a compound containing two different elements. Such binary compound may be, e.g., a Group II-VI semiconductor, a Group III-V semiconductor, a Group IV-VI semiconductor, a Group IV-IV semiconductor, a metal oxide, or a metal sulfide.

Examples of Group II-VI semiconductor materials include, without being limited to, cadmium selenide (CdSe), cadmium sulfide (CdS), cadmium telluride (CdTe), zinc selenide (ZnSe), zinc sulfide (ZnS), zinc telluride (ZnTe), mercury selenide (HgSe), mercury sulfide (HgS), and mercury telluride (HgTe); examples of Group III-V semiconductor materials include, without limiting, boron nitride (BN), boron phosphide (BP), boron arsenide (BAs or $B_{12}As_2$), aluminium nitride (AlN), aluminium phosphide (AlP), aluminium arsenide (AlAs), aluminium antimonide (AlSb), gallium nitride (GaN), gallium phosphide (GaP), gallium arsenide (GaAs), gallium antimonide (GaSb), indium nitride (InN), indium phosphide (InP), indium arsenide (InAs), and indium antimonide (InSb); examples of Group IV-VI semiconductor materials include, without being limited to, lead selenide (PbSe), lead sulfide (PbS), lead telluride (PbTe), tin sulfide (SnS or $SnS_2$), tin telluride (SnTe); and examples of Group IV-IV semiconductor materials include, without limiting, silicon carbide (SiC).

Examples of metal oxides include, without being limited to, zinc oxide (ZnO), cadmium oxide (CdO), lead oxide (PbO), molybdenum dioxide ($MoO_2$), silver oxide ($Ag_2O$), sodium oxide ($Na_2O$), mendelevium oxide (MeO), selenium dioxide ($SeO_2$), and iron(III) oxide ($Fe_2O_3$); and examples of metal sulfides include, without limiting, cadmium sulfide (CdS), lead sulfide (PbS), molybdenum disulfide ($MoS_2$), silver sulfide ($Ag_2S$), sodium sulfide ($Na_2S$), zinc sulfide (ZnS), mendelevium sulfide (MeS), selenium disulfide (SeS2), and iron disulfide (FeS$_2$).

In other particular such embodiments, the semiconductor material is a ternary compound, i.e., a compound containing three different elements. Non-limiting examples of such semiconductor materials include indium gallium arsenide (InGaAs), indium manganese arsenide (InMnAs), cadmium manganese telluride (CdMnTe), lead manganese telluride (PbMnTe), lead tin telluride (PbSnTe), lead selenide telluride (PbSeTe), lead selenide sulfide (PbSeS), lead telluride sulfide (PbTeS), thalium manganese arsenide (Tl$_2$GeTe$_5$), gallium manganese arsenide (GaMnAs), and zinc silicon phosphide (ZnSiP$_2$).

In certain embodiments, the semiconductor material composing the semiconductor crystals of the present invention is an element of Group XIV of the periodic table such as silicon and germanium.

According to the present invention, the band gap energy of the semiconductor material can be engineered by incorporation of amino acid molecules, peptides, or any combinations thereof, within the crystal lattice of the semiconductor crystals.

The term "amino acid" as used herein refers to an organic compound comprising both amine and carboxylic acid functional groups, which may be either a natural or non-natural amino acid. The twenty two natural amino acids are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of non-natural amino acids include diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine. According to the present invention, the band gap energy of the semiconductor material can be tuned by incorporation of molecules of either a particular amino acid or a combination of any two or more, i.e., two, three, four or more, amino acids.

The term "peptide" as used herein refers to a short chain of amino acid monomers linked by peptide bonds, i.e., the covalent bond formed when a carboxyl group of one amino acid reacts with an amino group of another. Such peptides, when consisting of more than 50 amino acid monomers, can also be classified as proteins, more particularly, proteins of low or medium molecular weight.

In certain embodiments, the peptides incorporated within the crystal lattice of the semiconductor crystals of the invention consist of 2-50, 2-40, 2-30, 2-20, 2-15, 2-10, or 2-5 amino acid residues. In more particular such embodiments, said peptides are dipeptides, tripeptides or tetrapeptides consisting of 2, 3 or 4 amino acid residues, respectively, or polypeptides consisting of 5, 6, 7, 8, 9, 10, 11 or 12 amino acid residues. All such peptides may consist of residues of amino acids as defined above, including both natural and non-natural amino acids.

In a particular study described herein, ZnO crystals were grown and precipitated from an aqueous solution containing $Zn^{2+}$ and $O^{2-}$ ions, in the presence of amino acid molecules (a different amino acid at each experiment), and as found, a reasonable number of the amino acids became incorporated at different levels into the ZnO lattice, with resulting lattice strains. The prepared samples were measured after mild heat treatment and all of them, except for cysteine and selenocysteine which contain S and Se atoms that chemically interact with the ZnO matrix, revealed lattice strain relaxation. Normalization of the strain values by nitrogen atomic percent indicated a strong correlation between shape change of the crystal and the measured strain, suggesting that amino acid which strongly interact with the ZnO host are more likely to be incorporated during the crystal growth. Measurement of the optical band gap of the amino acid-incorporating ZnO crystals before and after thermal annealing revealed that the band gap of those crystals was altered due to the amino acid incorporation, and that there is a linear relationship between the magnitude of strain induced by the incorporation and the change in the band gap of the ZnO crystalline host. In particular, while the band gap energy for the reference ZnO sample was 3.28 eV, ZnO incorporating cysteine exhibited the highest band gap increase, resulting in a band gap value of 3.41 eV, which was 4% higher than that of the reference sample.

The study described above clearly shows that amino acids can be incorporated into inorganic crystalline hosts other than calcite, in the present case specifically ZnO, and that incorporation of amino acids into an inorganic crystalline semiconductor host induces not only lattice strains, as previously observed in both biogenic and biomimetic calcium carbonate, but also a considerable band gap shift. In most cases, the incorporation of the amino acid tested led to an increase in the band gap compared to that of the reference sample. This unprecedented observation is most interesting, and could herald a new and bio-inspired route, in addition to and in combination with other methods currently available, for tuning of the band gaps of semiconductors.

At this point, the exact mechanism by which the incorporated amino acids alter the ZnO band gap is unclear, and it seems that further studies are required so as to understand this phenomenon. Nevertheless, it seems that the state of lattice strain observed in the study described herein is definitely different from that seen in conventional epitaxial strain-induced band gap engineering wherein a thin film is grown on a suitable substrate, which induces lattice strain via lattice mismatch. Owing to the Poisson effect, i.e., the tendency of a material compressed in one direction to expand in the other two directions perpendicular to the direction of compression, the strain within the plane of the layer is opposite in sign to the strain perpendicular to it, meaning that if the induced strain within the layer is positive, the perpendicular strain is negative. In ZnO, a positive strain along the a-axis leads to a decrease in the band gap (Yadav et al., 2010). The strain state in the present case is quite different, as along both the a and the c axes the strain is positive indicating lattice expansion in all crystallographic directions. In addition to this unexpected finding, it should be noted that the strain is not mechanical like it is in the case of epitaxial strain. In order to provide a direct explanation for the observed band gap shift via the induced strain, extensive study of the different molecular bond lengths, in combination with atomistic modeling, should be carried out.

One possible explanation for the band gap shift might be related to the number of oxygen vacancies in the ZnO lattice. It has been shown that as the number of oxygen vacancies decreases the band gap increases (Liu et al., 2013). Moreover, reaction of ZnO crystals with an oxidizing or a reducing environment proved that this change was reversible (Peng et al., 2013). It is therefore feasible that the amino acids become incorporated within the ZnO lattice at oxygen-deficient locations, thereby effectively lowering the relative amount of oxygen vacancies, which in turn increases the band gap. Another possible explanation for the shift in the band gap is that the incorporated organic molecules simply increase the effective dielectric constant of ZnO/amino acid composite crystals which, at least theoretically, should in turn increase the band gap.

In another study described herein, CdS crystals were grown and precipitated from an aqueous solution containing $Cd^{2+}$ ions and amino acid molecules (a different amino acid at each experiment), in the presence of solid NaSH as a source for $S^{2-}$ ions. Since CdS has a band gap energy in the visible energy range, the change in the band gap energy following incorporation of each one of the different amino acids was visible and clear. As shown in a particular experiment, CdS crystals precipitated from aqueous solutions containing different concentrations of histidine have different colors, reflecting the different band gap energy of the CdS crystals in each case.

In a further study described herein, PbS crystals were grown and precipitated from an aqueous solution containing $Pb^{2+}$ ions and amino acid molecules (a different amino acid at each experiment), in the presence of solid NaSH as a source for $S^{2-}$ ions. As found, a reasonable number of the amino acids became incorporated at different levels into the PbS lattice, with resulting lattice strains suggesting a band gap variation. The prepared samples were measured after mild heat treatment and all of them revealed lattice strain relaxation.

In certain embodiments, the semiconductor crystal of the present invention comprises a semiconductor crystal having a band gap energy and amino acid molecules incorporated within the crystal lattice, wherein the semiconductor material is a binary compound selected from a Group II-VI semiconductor, a Group III-V semiconductor, a Group IV-VI semiconductor, a Group IV-IV semiconductor, a metal oxide, or a metal sulfide, or a ternary compound selected from InGaAs, InMnAs, CdMnTe, PbMnTe, PbSnTe, PbSeTe, PbSeS, PbTeS, $Tl_2GeTe_5$, GaMnAs, or $ZnSiP_2$; and said amino acid is cystein, selenocystein, lysine, tyrosine, serine, histidine, arginine, or a combination thereof. Particular such embodiments are those wherein the semiconductor material is a metal oxide, e.g., ZnO, or a metal sulfide, e.g., CdS or PbS, wherein molecules of amino acid selected from cystein, selenocystein, lysine, tyrosine, serine, histidine, arginine, or a combination thereof are incorporated within the crystal lattice.

In another aspect, the present invention provides a method for the preparation of semiconductor crystals each as defined above, wherein said semiconductor material consists of two or more elements, said method comprising the steps of:
(i) precipitating said semiconductor crystals from either
(a) an aqueous solution containing said amino acid molecules, peptides, or combination thereof, and ions of said two or more elements; or (b) an aqueous solution containing said amino acid molecules, peptides, or combination thereof, and ions of at least one of said two or more elements, in the presence of precursors of the other of said two or more elements; and (ii) collecting the obtained semiconductor crystals, e.g., by filtration or drying of the aqueous solution.

The precipitation of the semiconductor crystals may be carried out from an aqueous solution containing ions of each one of the chemical elements composing the semiconductor material as well as the amino acid molecules, peptides, or combination thereof. In a particular such case exemplified herein, ZnO crystals were precipitated from an aqueous solution containing $Zn(NO_3)_2$ and $NH_4OH$ solution, each time in the presence of a different one of the 21 natural amino acids. Specifically, the amino acid was added with stirring to an aqueous solution of $Zn(NO_3)_2$ in the concentration range of 0.3 to 6 mg/ml, and to initiate crystallization, 1 ml of $NH_4OH$ was then added in drops to 100 ml of solution. Stirring was avoided to prevent early crystallization. The solution was transferred to a flask, immersed in a silicon oil bath, and kept at 95° C. while stirring for 1 hour. The resulting ZnO powders were washed several times with deionized water and air dried.

Alternatively, precipitation of the semiconductor crystals may be carried out from an aqueous solution containing ions of at least one of the chemical elements composing the semiconductor material as well as the amino acid molecules, peptides, or combination thereof, in the presence of precursors of the other chemical element(s) composing the semiconductor material. In particular such cases exemplified herein, CdS and PbS crystals were precipitated from an aqueous solution containing $CdCl_2$ or $PbCl_2$, respectively, and amino acid molecules, in the presence of solid NaSH. Specifically, the amino acid was added to an aqueous solution of $CdCl_2$ or $PbCl_2$, and the solution was placed in a desiccator in the presence of solid NaSH. To initiate crystallization, diluted HCl was added in drops, followed by the reaction of $CdCl_2$ or $PbCl_2$ with $H_2S$ evaporated from the reaction between NaSH and HCl. The resulting CdS and PbS powders were filtered, washed several times with deionized water and air dried.

It should be understood that in certain cases, such as those exemplified herein, the pH of the aqueous solution from which the semiconductor crystals are precipitated should be adjusted, prior to reaction, to a particular level/value (by the addition of an acid such as HCl or a base such as $NH_4OH$, as required), so as to limit, more precisely minimize, the ability of the functional groups of the amino acid, i.e., the amino group, the carboxyl group, or a functional group on the side chain, if present, to interact with ions of one or more of the chemical elements composing the semiconductor material.

In one embodiment, the method disclosed is for the preparation of semiconductor crystals as defined above, wherein the semiconductor material is a binary compound, said method comprising the steps of:
(i) preparing an aqueous solution containing ions of the first element of said semiconductor material;
(ii) adding said amino acid molecules, peptides, or combination thereof to said solution optionally while stirring;
(iii) precipitating said semiconductor crystals by either addition of ions of the second element of the semiconductor material or in the presence of a precursor of the second element of said semiconductor material; and
(iv) collecting the obtained semiconductor crystals.

In particular such embodiments, the method of the invention is for the preparation of such semiconductor crystals, wherein the first element of said binary compound is Cd, Hg, Zn, In, Ga, Al, Pb, Si, Mo, Ag, Na, Me, Se, or Fe, and the second element of said binary compound is Se, Te, S, N, P, As, Sb, C, or O. In more particular such embodiments, the first element of said binary compound is Zn and the second element of said binary compound is O; or the first element of said binary compound is Cd or Pb, and the precursor of the second element of said binary compound is a compound capable of providing $S^{2-}$ ions, such as NaSH.

In another embodiment, the method disclosed is for the preparation of semiconductor crystals as defined above, wherein the semiconductor material is a ternary compound, said method comprising the steps of:
(i) preparing an aqueous solution containing ions of two of the elements of said semiconductor material;
(ii) adding said amino acid molecules, peptides, or combination thereof to said solution optionally while stirring;
(iii) precipitating said semiconductor crystals by either addition of ions of the third element of the semiconductor material or in the presence of a precursor of the third element of said semiconductor material; and
(iv) collecting the obtained semiconductor crystals.

The method of the present invention can also be seen as an improvement of a method for the preparation of semiconductor crystals aimed at tuning, i.e., engineering, the band gap energy of the semiconductor material of which said semiconductor crystals are made. More particularly, according to the invention, in a method for the preparation of semiconductor crystals comprising a semiconductor material having a band gap energy, the improvement wherein amino acid molecules, peptides, or a combination thereof are incorporated with said semiconductor material, within the crystal lattice, to thereby tune said band gap energy. In particular embodiments, the semiconductor material composing said semiconductor crystals consists of two or more elements, e.g., is a binary compound or a ternary compound as defined above.

The invention will now be illustrated by the following non-limiting Examples.

EXAMPLES

Experimental

Materials. ZnO crystals were crystallized from zinc nitrate hexahydrate (Scharlau Chemie, Spain) and ammonium hydroxide solution (Bio-Lab, Israel), wherein hydrochloric acid 37% (Merck) was used for pH control. CdS crystals were crystallized from cadmium chloride hemi (pentahydrate) and sodium hydrosulfide hydrate both perched from Sigma-Aldrich, wherein potassium hydroxide (Bio-Lab, Israel) and hydrochloric acid 37% (Merck) were used for pH control. The 21 amino acids used were L-aspartic acid (Asp), DL-tyrosine (Tyr), L-leucine (Leu), L-tryptophan (Trp), L-arginine (Arg), L-valine (Val), L-glutamic acid (Glu), L-methionine (Met), D-phenylalanine (Phe), DL-serine (Ser), D-alanine (Ala), L-glutamine (Gln), glycine (Gly), DL-proline (Pro), L-threonine (Thr), L-asparagine (Asn), L-lysine (Lys), L-histidine (His), L-isoleucine (Ile), L-cysteine (Cys), and seleno-L-cysteine (Sec), all purchased from Sigma-Aldrich. Deionized water was used for all the solutions.

ZnO Crystal growth. ZnO powders were precipitated from aqueous solution containing $Zn(NO_3)_2$ (0.25 M) and pure ammonium hydroxide solution, in the presence of each of the 21 amino acids. Each amino acid was added with stirring to an aqueous solution of $Zn(NO_3)_2$ in the concentration range of 0.3 to 6 mg/ml. In all samples the pH was adjusted to 6 prior to reaction by addition of $NH_4OH$ or HCl. To initiate crystallization, 1 ml of $NH_4OH$ was added in drops to 100 ml of solution. Stirring was avoided to prevent early crystallization. The solution was transferred to a flask, immersed in a silicon oil bath, and kept at 95° C. while stirring for 1 hour. The resulting ZnO powders were washed several times with Deionized water and air dried. Reference ZnO samples were prepared by the same method without amino acids.

CdS Crystal growth. CdS powders were precipitated from aqueous solution containing $CdCl_2$ (0.015 M) in the presence of each of the 21 amino acids. Each amino acid was added to the aqueous solution of $CdCl_2$ in the concentration range of 0.3 to 6 mg/ml. In all samples the pH was adjusted to 5 prior to reaction by addition of KOH or HCl. The aqueous solution of $CdCl_2$ was placed in a desiccator in the presence of solid NaSH (0.1 gr). To initiate crystallization, 10 ml of diluted HCl (18.5%) was added in drops using an ISMATEC peristaltic tubing pump at a pumping rate of 0.1 ml/min. In this process, the crystals were precipitated in a $CdCl_2$ solution due to the presence of $H_2S$ gas evaporated from the reaction between NaSH and HCl. After the dropping finished (about 100 min) the resulting CdS powders were filtered, washed several times with deionized water and air dried. Reference CdS samples were prepared by the same method without amino acids.

PbS Crystal growth. PbS powders were precipitated from 0.015 M $PbCl_2$ and dissolved in deionized water solution under a constant stirring and placed in a desiccator. A hydrochloric acid (HCl) solution (6M) was added drop by drop by a syringe pump at the rate of 0.1 ml/min over 0.1 gr of pure NaSH. In each experiment, a different amino acid was added to the $Pb^{2+}$ solution at concentrations ranging between 3 and 6 mg/ml. Before the beginning of the experiment, the pH of the solution was stabilized to pH 6 by the addition of 6 M HCl or 24%-30% w/w ammonium hydroxide as required. The resulting PbS powders were filtered using standard filter paper, washed several times with deionized water and then air dried for 24 hours. Reference PbS samples were prepared in the same way but without the addition of amino acids to the solution.

Characterization of ZnO crystals.

The powders were characterized by high-resolution powder X-ray diffraction (HR-XRD) utilizing a synchrotron source. Diffraction measurements were conducted on ID31 of the European Synchrotron Research Facility (ESRF), Grenoble, France, at a wavelength of 0.476798 Å±0.000008 Å. ZnO lattice parameter values were deduced by the Rietveld refinement method (using the GSAS program, EXPGUI interface). To determine the intracrystalline amino acid concentration, samples were analyzed by X-ray photoemission spectroscopy (XPS). Optical band gap was established by diffuse reflectance measurements using the Cary 5000 UV-Vis-NIR spectrophotometer (Agilent Technologies) with a DRA-2500 integrating sphere attachment. Optical reflection was obtained over a range of 250 to 800 nm.

Example 1

Figure 1B:
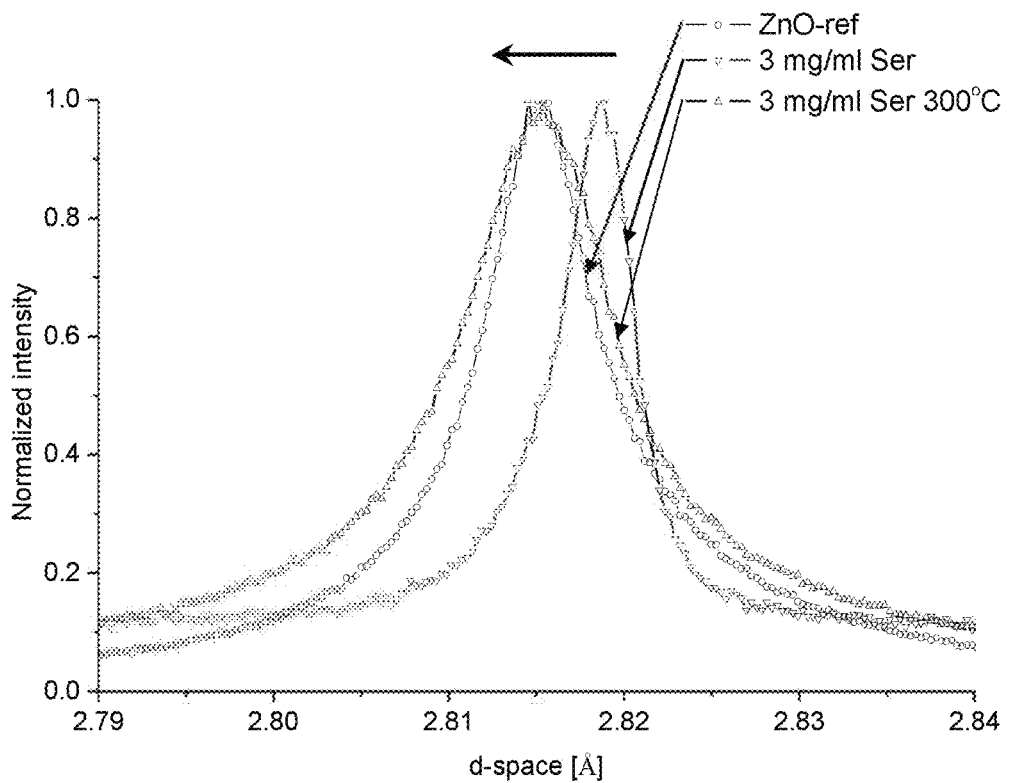

In order to determine whether amino acids would be able to become incorporated into the lattice of ZnO, as previously shown for calcite (Borukhin et al., 2012), ZnO was grown in the presence of the various amino acids at different solution concentrations. In a test case, the amino acid serine was used, and as found, serine indeed became incorporated and induced lattice strains of up to about 0.2% in the ZnO host, with a linear correlation between the level of incorporation and the lattice strain induced (FIG. 1A). Moreover, similarly to what previously observed in both biogenic and biomimetic calcite, these strains relaxed upon mild thermal air annealing (300° C. for 90 min), and a unique microstructure developed, characterized by broadening of the diffraction peaks (FIG. 1B). Such broadening was unlike the pattern found under similar circumstances in most conventional materials, where the diffraction peaks are narrowed due to crystal growth and defect annealing, but was similar to what previously observed in biogenic crystals (Pokroy et al., 2006c).

Example 2

Figure 2A:
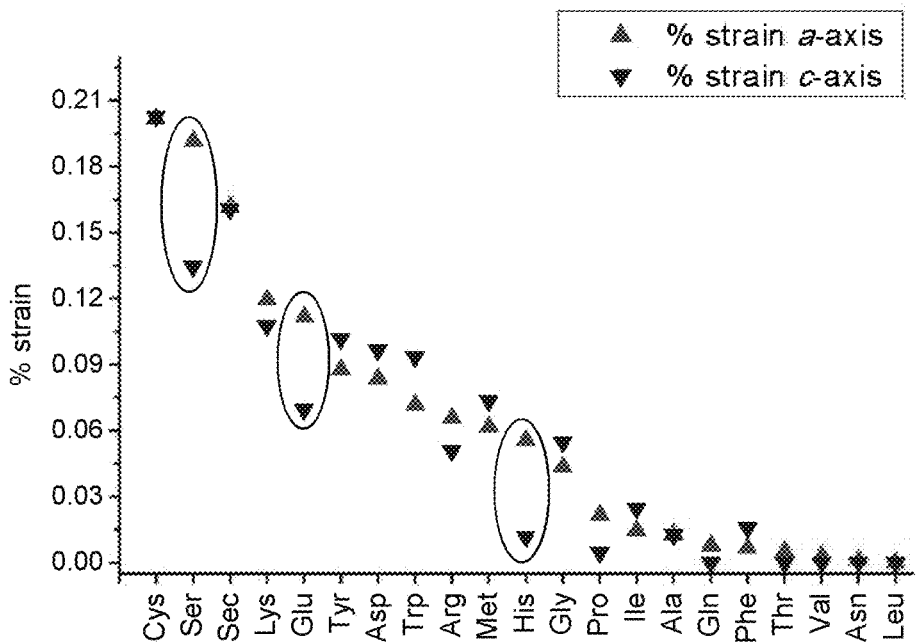
FIGS. 2A-2B show lattice strain of ZnO incorporated with different amino acids along the a-axis and along the c-axis, wherein circles indicate anisotropic strain (2A); and lattice strain normalized by intracrystalline amino acid concentration, wherein the geometric shapes schematically represent the rod-like, sphere-like or star-like crystal shapes received during the crystallization process (2B).

In the present study we screened the ability of all the common amino acids to incorporate into the ZnO lattice, and as found, a reasonable number of those amino acids indeed became incorporated at different levels into the ZnO lattice, with resulting lattice strains (FIG. 2A). As with serine, all samples were measured after mild heat treatment as well, and as shown in Table 1, all of them except for cysteine and selenocysteine revealed lattice strain relaxation. The fact that no lattice relaxation was observed after annealing at 300° C. for 90 min in the cases of cysteine and selenocysteine is most probably due to the presence of S or Se atom in these amino acids. These atoms interact with the ZnO lattice and therefore, a higher annealing temperature is required.

Amino acid concentrations were estimated by XPS analysis to detect the atomic percentage of intracrystalline nitrogen (N) corresponding to the intracrystalline amino acid concentration. Amino acids at. % conformed by energy dispersive spectroscopy (EDS) over a cross-section of ZnO incorporated with cysteine. In the latter case, at. % of S was detected and revealed similar values to the XPS results.

Figure 2B:
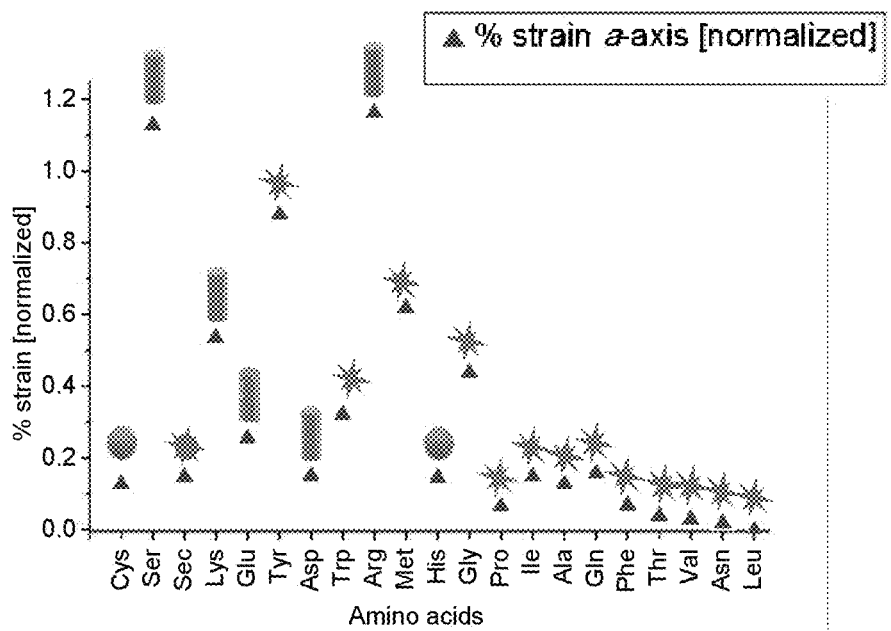

For each amino acid, the strain value was normalized by N at. % (FIG. 2B). Strain values for samples in which the nitrogen concentration was below the detection limit (~0.1 at. %) were normalized to the detection limit concentration. No nitrogen was detected in the reference ZnO sample, which was grown in the absence of amino acids. FIG. 2B indicates a strong correlation between shape change of the crystal and the measured strain, indicating that amino acid which strongly interact with the ZnO host are more likely to be incorporated during the crystal growth. Among those amino acids are those with an electrically charged side chain, i.e., Lys, Asp and Glu, a polar side chain, i.e., Ser and Tyr, and special amino acids with atoms chemically interacting with ZnO, i.e., Cys and Sec. Interestingly, the highest incorporation level was shown in the case of serine and arginine.

The results above clearly demonstrate that incorporation of amino acids into other crystalline materials is feasible. Furthermore, the findings of this study may have a considerable impact on tuning the properties of new functional materials. In the present case, because ZnO is a semiconductor, we expected that the incorporation of organic molecules within the host lattice and the resulting lattice strain induction would alter the electronic properties as compared to pure ZnO crystals. We therefore measured the optical band gap of our amino acid-incorporating ZnO crystals. To quantify the band gap energy we obtained reflection spectra of the ZnO powders from diffused reflectance spectroscopy combined with the Kebulka-Munk (K-M) method (Kubelka and Munk, 1931; Simmons, 1976).

TABLE 1

Quantitative data regarding amino acid content in the reaction solution, strain induced for each amino acid in both a and c- axes before and after thermal annealing (bold), and the atomic percent (at. %) of intracrystalline amino acids found by dividing the N at. % by the number of N atoms in the molecule

| Incorporated amino acid | Amino acid concentration [mg/ml] | % strain a-axis | % strain c-axis | Rietveld refinement goodness of fit: $\chi^2$ | At. % of incorporated amino acid |
|---|---|---|---|---|---|
| Asp | 0.3 | 0.084 | 0.097 | 1.635 | 0.55 |
|  |  | 0.001 | 0 | 1.308 |  |
| Glu | 3 | 0.112 | 0.07 | 2.889 | 0.44 |
|  |  | 0.019 | 0.013 | 1.439 |  |
| Cys | 0.5 | 0.202 | 0.203 | 1.764 | 1.56 |
|  |  | 0.243 | 0.233 | 1.635 |  |
| Sec | 0.5 | 0.166 | 0.161 | 1.631 | 1.09 |
|  |  | 0.099 | 0.208 | 1.573 |  |
| Ser | 3 | 0.104 | 0.031 | 1.876 | 0.17 |
|  |  | 0.007 | 0.001 | 1.006 |  |
| Lys | 4 | 0.120 | 0.108 | 3.457 | 0.23 |
|  |  | 0.009 | 0.014 | 4.437 |  |
| Gly | 1 | 0.044 | 0.055 | 1.745 | <0.1 |
|  |  | 0.007 | 0.008 | 1.606 |  |
| Tyr | 0.5 | 0.088 | 0.102 | 2.304 | <0.1 |
|  |  | 0.012 | 0.008 | 1.324 |  |
| Trp | 1 | 0.072 | 0.094 | 1.935 | 0.23 |
|  |  | 0.004 | 0.004 | 1.26 |  |
| Arg | 4 | 0.066 | 0.051 | 1.42 | 0.06 |
| His | 1 | 0.056 | 0.012 | 4.667 | 0.38 |
| Met | 3 | 0.061 | 0.074 | 1.65 | <0.1 |
| Pro | 3 | 0.022 | 0.005 | 3.731 | 0.33 |
| Ala | 3 | 0.013 | 0.013 | 3.36 | <0.1 |
| Leu | 1 | 0.001 | 0.014 | 3.482 | <0.1 |
| Ile | 3 | 0.015 | 0.025 | 4.035 | <0.1 |
| Val | 3 | 0.003 | 0.042 | 4.574 | <0.1 |
| Phe | 3 | 0.007 | 0.016 | 3.824 | <0.1 |
| Thr | 1 | 0.005 | 0.011 | 4.091 | 0.125 |

TABLE 1-continued

Quantitative data regarding amino acid content in the reaction solution, strain induced for each amino acid in both a and c- axes before and after thermal annealing (bold), and the atomic percent (at. %) of intracrystalline amino acids found by dividing the N at. % by the number of N atoms in the molecule

| Incorporated amino acid | Amino acid concentration [mg/ml] | % strain a-axis | % strain c-axis | Rietveld refinement goodness of fit: $\chi^2$ | At. % of incorporated amino acid |
|---|---|---|---|---|---|
| Asn | 1 | 0.001 | 0.002 | 3.043 | <0.1 |
| Gln | 1 | 0.008 | 0.05 | 4.878 | <0.1 |

Figure 3A:
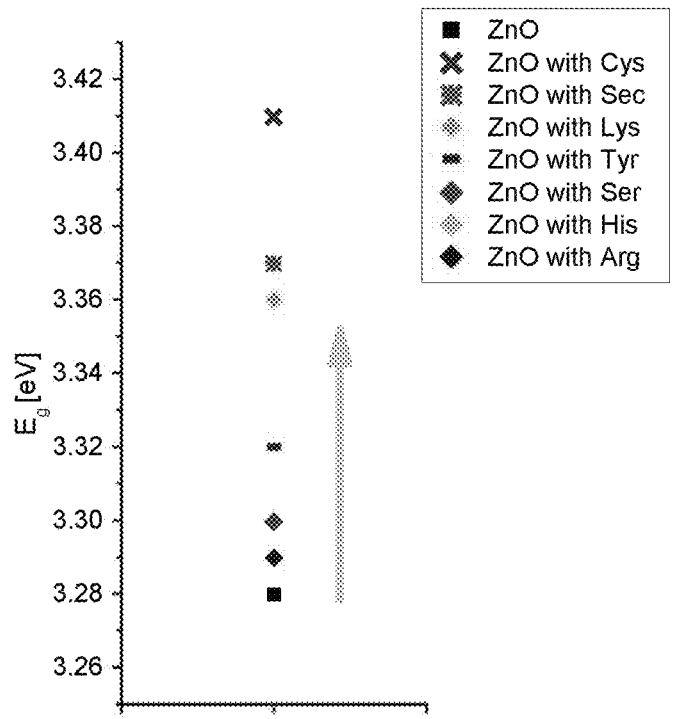
FIGS. 3A-3B show band gap values (3A) and band gap energy change ($\Delta E_g$, difference between before and after annealing) (3B) as a function of c-axis strain of ZnO samples crystallized in the presence of different amino acids.
Figure 3B:
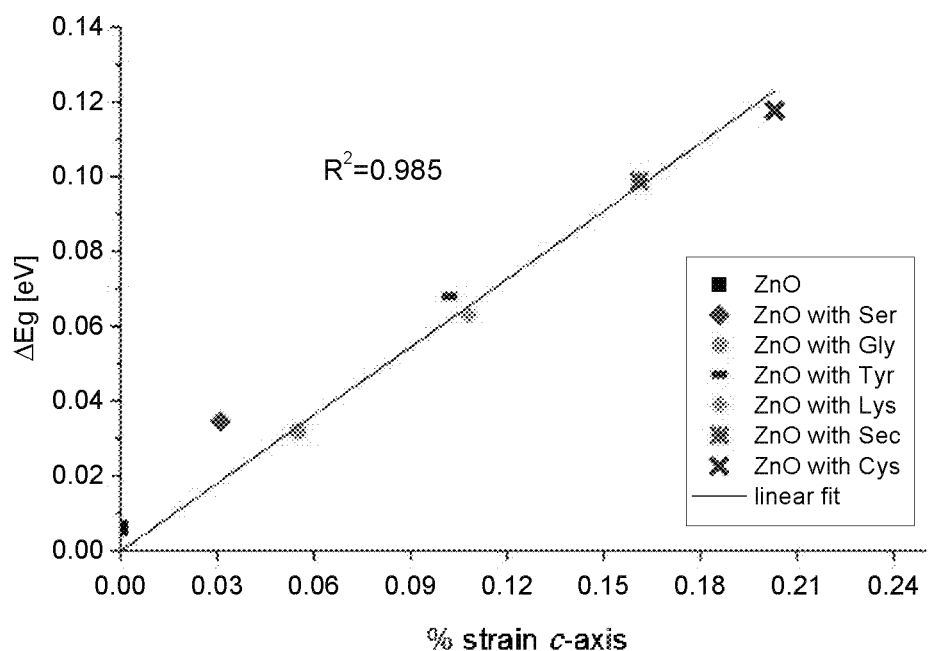

Using this method, we measured the changes in the band gap energy (ΔEg) for different amino acid-incorporating ZnO crystals before and after thermal annealing, and for various crystals possessing different levels of induced lattice strains, and as observed, the band gap was indeed altered due to the amino acid incorporation (FIG. 3A) and moreover, there was a linear relationship between the magnitude of strain induced by the incorporation and the change in the band gap of the ZnO crystalline host (FIG. 3B).

In order to verify that the change in band gap was indeed caused by the incorporated amino acids, we measured the band gap on the same samples after mild thermal annealing, which also leads to full strain relaxation, and found that the band gap indeed returned to levels close to the control sample. In contrast, the band gap value of the reference ZnO remained almost the same after thermal annealing at 300° C. For the reference ZnO samples the average band gap energy was 3.28 eV, which corresponds with previously reported values of 3.2-3.4 eV (Srikant and Clarke, 1998; Reynolds et al., 1999). ZnO samples incorporating cysteine exhibited the highest band gap increase, resulting in a band gap value of 3.41 eV, which was 4% higher than the band gap of the reference sample. For most of the amino acids, a positive linear correlation between band gap change and intracrystalline strain was observed ($R^2=0.98$) (FIG. 3B).

Example 3

Figure 4:
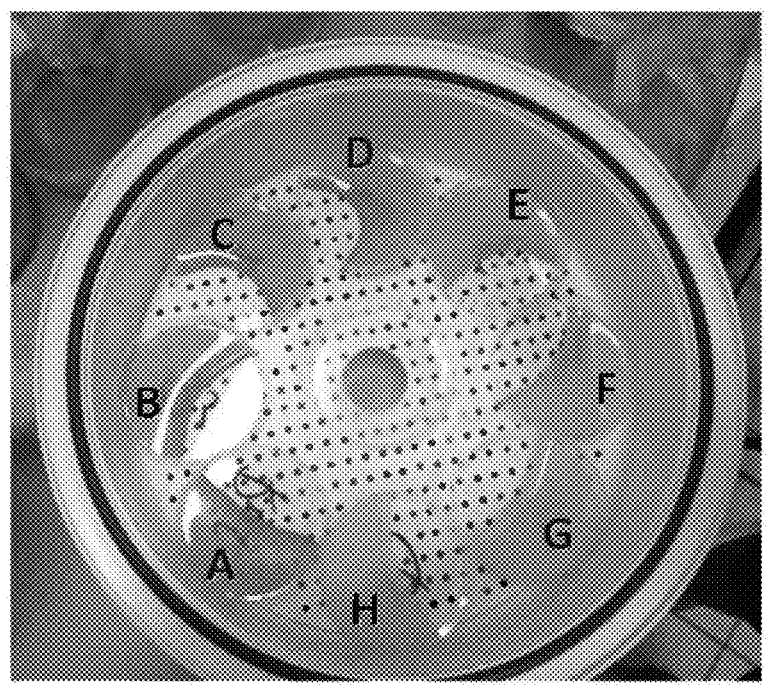
FIG. 4 shows CdS samples having different colors, prepared by precipitation from aqueous solutions containing different concentrations of histidine, reflecting the different band gap energies of those samples as compared to that of the reference sample. Reference sample without histidine (A); Samples precipitated from aqueous solution containing 0.5 mg/ml (B), 1 mg/ml (C), 2 mg/ml (D), 3 mg/ml (E), 4 mg/ml (F), 5 mg/ml (G), and 6 mg/ml (H) histidine.

In this study, CdS crystals with engineered band gap energy were prepared as described in Experimental, by precipitation from aqueous solutions containing different concentrations of histidine, while reference CdS samples were prepared by the same method without the amino acid. FIG. 4 shows CdS samples having different colors, prepared by precipitation from aqueous solutions containing different concentrations of histidine, reflecting the different band gap energies of those samples as compared to that of the reference sample.

Example 4

Figure 5:
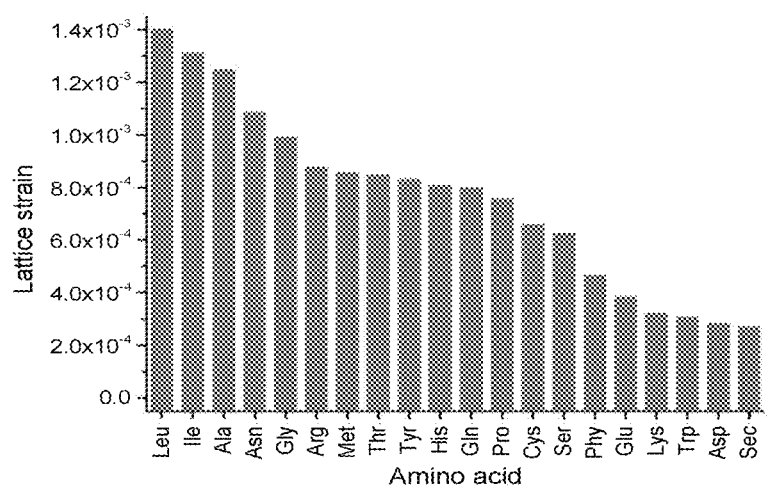
FIG. 5 shows lattice strain of PbS with incorporated amino acids.

Similarly to the ZnO samples, the lattice distortion of PbS crystals was calculated by applying the Rietveld refinement method over the high-resolution diffraction spectrum taken form PbS crystals on the ID31 beamline of the ESRF. The whole spectrum was collected within an angular interval of 0<2θ<35° at a wavelength of 0.39985 Å. All the observed reflections indicated a single phase of cubic PbS. When comparing PbS synthesized in the presence of amino acids to the reference sample, a significant shift in the diffraction peak position was noticed, indicating lattice distortion or lattice strain. These lattice distortions, as in the case of ZnO and $CaCO_3$, show that amino acids were incorporated into the crystal structure of PbS. After mild thermal annealing at 150° C. for 90 minutes, full relaxation of the lattice was noticed due to amino acid decomposition. The highest strain values were measured for leucine, isoleucine and alanine incorporation. In spite of the fact that these amino acids are non-charged and hydrophobic, this result is not surprising and similar to the case of crystallization in the presence of surfactants in water. Due to their hydrophobic nature, these molecules adopt a special arrangement on the inorganic surfaces that maximize the hydrophobic interaction between the hydrocarbon tails and minimize the interaction with the water. This phenomenon can increase the incorporation probability, and as a result, the amount of amino acids incorporated (FIG. 5).

REFERENCES

Aizenberg, J., Hanson, J., Koetzle, T. F., Leiserowitz, L., Weiner, S., Addadi, L., *Chem-Eur J.*, 1995, 1, 414

Aizenberg, J., Ilan, N., Weiner, S., Addadi, L., *Connect. Tissue Res.*, 1996, 35, 17 Berman, A., Addadi, L., Kvick, A., Leiserowitz, L., Nelson, M., Weiner, S., *Science*, 1990, 250, 664

Berman, A., Hanson, J., Leiserowitz, L., Koetzle, T. F., Weiner, S., Addadi, L., *Science*, 1993, 259, 776

Berman, A., Addadi, L., Weiner, S., *Nature*, 1988, 331, 546

Borukhin, S., Bloch, L., Radlauer, T., Hill, A. H., Fitch, A. N., Pokroy, B., *Adv. Funct. Mater.*, 2012, 22, 4216

Capasso, F., *Science*, 1987, 235, 172

Chernov, A. A., *J. Struct. Biol.*, 2003, 142, 3

Dunlop, J. W. C., Fratzl, P., *Annu. Rev. Mater. Res.*, 2010, 40, 1

Estroff, L. A., *Chem. Rev.*, 2008, 108, 4329

Fratzl, P., Weinkamer, R., *Prog. Mater. Sci.*, 2007, 52, 1263

Gower, L. B., *Chem. Rev.*, 2008, 108, 4551

Guoqiang, Q., Guanglei, Z., Dongchun, L., Shimin, L., *Thin Solid Films*, 2010, 519, 378

Kim, Y. Y., Ribeiro, L., Maillot, F., Ward, O., Eichhorn, S. J., Meldrum, F. C., *Adv. Mater.*, 2010, 22, 2082

Kim, Y. Y., Ganesan, K., Yang, P., Kulak, A. N., Borukhin, S., Pechook, S., Ribeiro, L., Kroger, R., Eichhorn, S. J., Armes, S. P., Pokroy, B., Meldrum, F. C., *Nat. Mater.*, 2011, 10, 890

Kirschvink, J. L., Gould, J. L., *Biosystems*, 1981, 13, 181

Kubelka, P., Munk, F., *Z. Tech. Phys.*, 1931, 12, 593

Levy-Lior, A., Pokroy, B., Levavi-Sivan, B., Leiserowitz, L., Weiner, S., Addadi, L., *Cryst. Growth Des.*, 2008, 8, 507

Levy-Lior, A., Shimoni, E., Schwartz, O., Gavish-Regev, E., Oron, D., Oxford, G., Weiner, S., Addadi, L., *Adv. Funct. Mater.*, 2010, 20, 320

Li, H. Y., Estroff, L. A., *Adv. Mater.*, 2009, 21, 470

Miserez, A., Weaver, J. C., Pedersen, P. B., Schneeberk, T., Hanlon, R. T., Kisailus, D., Birkedal, H., *Adv. Mater.*, 2009, 21, 401

Muñoz-Espí, R., Qi, Y., Lieberwirth, I., Gomez, C. M., Wegner, G., *Chem. Eur. J.*, 2006, 12, 118-129

Muñoz-Espí, R., Jeschke, G., Lieberwirth, I., Gómez, C. M., Wegner, G., *J. Phys. Chem. B*, 2007, 111, 697-707

Picker, A., Kellermeier, M., Seto, J., Gebauer, D., Colfen, H., *Z. Kristallogr.*, 2012, 227, 744

Pokroy, B., Quintana, J. P., Caspi, E. N., Berner, A., Zolotoyabko, E., *Nat. Mater.*, 2004, 3, 900

Pokroy, B., Fitch, A. N., Lee, P. L., Quintana, J. P., Caspi, E. N., Zolotoyabko, E., *J. Struct. Biol.*, 2006a, 153, 145

Pokroy, B., Fitch, A. N., Marin, F., Kapon, M., Adir, N., Zolotoyabko, E., *J. Struct. Biol.*, 2006b, 155, 96

Pokroy, B., Fitch, A. N., Zolotoyabko, E., *Adv. Mater.*, 2006c, 18, 2363

Reynolds, D. C., Look, D. C., Jogai, B., Litton, C. W., Cantwell, G., Harsch, W. C., *Phys. Rev. B*, 1999, 60, 2340

Schenk, A. S., Zlotnikov, I., Pokroy, B., Gierlinger, N., Masic, A., Zaslansky, P., Fitch, A. N., Paris, O., Metzger, T. H., Colfen, H., Fratzl, P., Aichmayer, B., *Adv. Funct. Mater.*, 2012, 22, 4668

Simmons, E. L., *Appl. Optics*, 1976, 15

Sommerdijk, N. A. J. M., de With, G., *Chem. Rev.*, 2008, 108, 4499

Srikant, V., Clarke, D. R., *J. Appl. Phys.*, 1998, 83, 5447

Weaver, J. C., Milliron, G. W., Miserez, A., Evans-Lutterodt, K., Herrera, S., Gallana, I., Mershon, W. J., Swanson, B., Zavattieri, P., DiMasi, E., Kisailus, D., *Science*, 2012, 336, 1275

Wei, S. H., Zunger, A., *Phys. Rev. B*, 1994, 49, 14337

Weiner, S., Addadi, L., *Annu. Rev. Mater. Res.*, 2011, 41, 21

Yadav, S. K., Sadowski, T., Ramprasad, R., *Phys. Rev. B*, 2010, 81, 144120

Liu, H., Zeng, F., Lin, Y., Wang, G., Pan, F., *Appl. Phys. Lett.*, 2013, 102, 181908

Peng, J.-W., Liu, P.-C., Lee, S., *Thin Solid Films*, 2013, 531, 81

The invention claimed is:

1. A semiconductor crystal comprising a semiconductor material having a band gap energy, and amino acid molecules, peptides, or a combination thereof, inside a crystal lattice of said semiconductor crystal, wherein said amino acid molecules, peptides, or combination thereof tune the band gap energy of said semiconductor material.

2. The semiconductor crystal of claim 1, wherein the band gap energy of said semiconductor material is in the infrared energy range, visible energy range, or the ultraviolet energy range.

3. The semiconductor crystal of claim 1, wherein said semiconductor material consists of two or more elements.

4. The semiconductor crystal of claim 3, wherein said semiconductor material is a binary compound.

5. The semiconductor crystal of claim 4, wherein said binary compound is a Group II-VI semiconductor, a Group III-V semiconductor, a Group IV-VI semiconductor, a Group IV-IV semiconductor, a metal oxide, or a metal sulfide.

6. The semiconductor crystal of claim 5, wherein said Group II-VI semiconductor is CdSe, CdS, CdTe, ZnSe, ZnS, ZnTe, HgSe, HgS, or HgTe; said Group III-V semiconductor is BN, BP, Bas, $B_{12}As_2$, AlN, AlP, AlAs, AlSb, GaN, GaP, GaAs, GaSb, InN, InP, InAs, or InSb; said Group IV-VI semiconductor is PbSe, PbS, PbTe, SnS, $SnS_2$, or SnTe; said Group IV-IV semiconductor is SiC; said metal oxide is ZnO, CdO, PbO, $MoO_2$, $Ag_2O$, $Na_2O$, MeO, $SeO_2$, or $Fe_2O_3$; and said metal sulfide is CdS, PbS, $MoS_2$, $Ag_2S$, $Na_2S$, ZnS, MeS, $SeS_2$, or $FeS_2$.

7. The semiconductor crystal of claim 3, wherein said semiconductor material is a ternary compound.

8. The semiconductor crystal of claim 7, wherein said ternary compound is InGaAs, InMnAs, CdMnTe, PbMnTe, PbSnTe, PbSeTe, PbSeS, PbTeS, $Tl_2GeTe_5$, GaMnAs, or $ZnSiP_2$.

9. The semiconductor crystal of claim 1, wherein said semiconductor material is an element of Group XIV of the periodic table.

10. The semiconductor crystal of claim 1, wherein said amino acid molecules, peptides, or combination thereof either increase or decrease the band gap energy of said semiconductor material.

11. The semiconductor crystal of claim 1, wherein said amino acid is a natural or non-natural amino acid, or said peptides each consisting of 2 to 12 natural or non-natural amino acid residues.

12. The semiconductor crystal of claim 11, wherein said natural amino acid each independently is selected from the group consisting of aspartic acid, tyrosine, leucine, tryptophan, arginine, valine, glutamic acid, methionine, phenylalanine, serine, alanine, glutamine, glycine, proline, threonine, asparagine, lysine, histidine, isoleucine, cysteine, and selenocysteine; and said non-natural amino acid each independently is selected from the group consisting of diaminopropionic acid, diaminobutyric acid, ornithine, aminoadipic acid, β-alanine, 1-naphthylalanine, 3-(1-naphthyl)alanine, 3-(2-naphthyl)alanine, γ-aminobutiric acid, 3-(aminomethyl)benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

13. The semiconductor crystal of claim 3, wherein said semiconductor material is a binary compound selected from the group consisting of a Group II-VI semiconductor, a Group III-V semiconductor, a Group IV-VI semiconductor, a Group IV-IV semiconductor, a metal oxide, and a metal sulfide, or a ternary compound selected from the group consisting of InGaAs, InMnAs, CdMnTe, PbMnTe, PbSnTe, PbSeTe, PbSeS, PbTeS, $Tl_2GeTe_5$, GaMnAs, and $ZnSiP_2$; and said amino acid is cystein, selenocystein, lysine, tyrosine, serine, histidine, arginine, or a combination thereof.

14. The semiconductor crystal of claim 13, wherein said semiconductor material is ZnO, CdS or PbS, and said amino acid is cystein, selenocystein, lysine, tyrosine, serine, histidine, arginine, or a combination thereof.

15. A method for the preparation of semiconductor crystals each according to claim 1, wherein said semiconductor material consists of two or more elements, said method comprising:
   (i) precipitating said semiconductor crystals from either
      (a) an aqueous solution containing said amino acid molecules, peptides, or combination thereof, and ions of said two or more elements; or (b) an aqueous solution containing said amino acid molecules, peptides, or combination thereof, and ions of at least one of said two or more elements, in the presence of precursors of the other of said two or more elements; and
   (ii) collecting the obtained semiconductor crystals.

16. A method for the preparation of semiconductor crystals each according to claim 1, wherein said semiconductor material is a binary compound, said method comprising:
  (i) preparing an aqueous solution containing ions of the first element of said semiconductor material;
  (ii) adding said amino acid molecules, peptides, or combination thereof to said solution;
  (iii) precipitating said semiconductor crystals by either addition of ions of the second element of the semiconductor material or in the presence of a precursor of the second element of said semiconductor material; and
  (iv) collecting the obtained semiconductor crystals.

17. A method for the preparation of semiconductor crystals each according to claim 1, wherein said semiconductor material is a ternary compound, said method comprising:
  (i) preparing an aqueous solution containing ions of two of the elements of said semiconductor material;
  (ii) adding said amino acid molecules, peptides, or combination thereof to said solution;
  (iii) precipitating said semiconductor crystals by either addition of ions of the third element of the semiconductor material or in the presence of a precursor of the third element of said semiconductor material; and
  (iv) collecting the obtained semiconductor crystals.

18. The method of claim 16, wherein the first element of said binary compound is Cd, Hg, Zn, In, Ga, Al, Pb, Si, Mo, Ag, Na, Me, Se, or Fe, and the second element of the binary compound is Se, Te, S, N, P, As, Sb, C, or O.

19. The method of claim 18, wherein the first element of said binary compound is Zn and the second element of said binary compound is O; or the first element of said binary compound is Cd or Pb, and the precursor of the second element of said binary compound is a compound capable of providing $S^{2-}$ ions.

20. The semiconductor crystal of claim 9, wherein said element of Group XIV of the periodic table is silicon or germanium.

21. The method of claim 19, wherein the precursor of the second element of said binary compound is NaSH.

* * * * *

UNITED STATES PATENT AND TRADEMARK OFFICE
CERTIFICATE OF CORRECTION

PATENT NO. : 9,771,263 B2
APPLICATION NO. : 14/500775
DATED : September 26, 2017
INVENTOR(S) : Boaz Pokroy It is certified that error appears in the above-identified patent and that said Letters Patent is hereby corrected as shown below:

On the Title Page

In Column 2 (item (56)) at Line 9 (approx.), Under Other Publications, change "Compund" to --Compound--.

In the Specification

In Column 5 at Line 11 (approx.), Change "thalium" to --thallium--.

In Column 5 at Line 38, Change "γ-aminobutiric" to --γ-aminobutyric--.

In Column 5 at Line 39, Change "p-propargly" to --p-propargyl--.

In Column 7 at Line 48, Change "cystein, selenocystein," to --cysteine, selenocysteine,--.

In Column 7 at Line 53, Change "cystein, selenocystein," to --cysteine, selenocysteine,--.

In Column 12 at Line 31, Change "Kebulka-" to --Kubelka- --.

In the Claims

In Column 15 at Line 64, In Claim 6, change "AIN," to --AlN,--.

In Column 16 at Line 8, In Claim 8, change "Tl$_2$GeTe$_5$," to --Tl$_2$GeTe$_5$,--.

In Column 16 at Line 31, In Claim 12, change "γ-aminobutiric" to --γ-aminobutyric--.

In Column 16 at Line 32, In Claim 12, change "p-propargly-" to --p-propargyl- --.

In Column 16 at Line 48, In Claim 13, change "Tl$_2$GeTe$_5$," to --Tl$_2$GeTe$_5$,--.

Signed and Sealed this
Twentieth Day of February, 2018

Andrei Iancu
*Director of the United States Patent and Trademark Office*

CERTIFICATE OF CORRECTION (continued)
U.S. Pat. No. 9,771,263 B2

In Column 16 at Line 49, In Claim 13, change "cystein, selenocystein," to --cysteine, selenocysteine,--.

In Column 16 at Line 53, In Claim 14, change "cystein, selenocystein," to --cysteine, selenocysteine,--.